United States Patent
Knerr et al.

(10) Patent No.: US 6,645,191 B1
(45) Date of Patent: Nov. 11, 2003

(54) MULTI-CHAMBER CONTAINER WITH A CONCENTRATED GLUCOSE COMPARTMENT AND A CONCENTRATED HYDROCHLORIC ACID COMPARTMENT

(75) Inventors: Thomas Knerr, St. Wendel (DE); Harald Pott, Illingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 135 days.

(21) Appl. No.: 09/714,873

(22) Filed: Nov. 17, 2000

(30) Foreign Application Priority Data

Nov. 18, 1999 (DE) .......................................... 199 55 578

(51) Int. Cl.[7] .............................................. A61B 19/00
(52) U.S. Cl. .......................... 604/410; 604/416; 604/89
(58) Field of Search ........................... 604/148, 82, 87, 604/88, 89, 90, 91, 403, 410, 415–16; 206/219

(56) References Cited

U.S. PATENT DOCUMENTS

| | | | |
|---|---|---|---|
| 4,202,760 A | | 5/1980 | Storey et al. |
| 4,336,881 A | * | 6/1982 | Babb et al. ................. 206/525 |
| 5,211,643 A | * | 5/1993 | Reinhardt et al. .......... 206/221 |
| 5,767,123 A | * | 6/1998 | Yoshida et al. ............. 514/276 |
| 5,944,709 A | * | 8/1999 | Barney et al. ............... 206/219 |
| 6,241,943 B1 | * | 6/2001 | Wieslander et al. ............ 422/1 |
| 6,309,673 B1 | * | 10/2001 | Duponchelle et al. ...... 424/677 |
| 6,426,056 B2 | * | 7/2002 | Taylor ......................... 422/261 |
| 2001/0044424 A1 | * | 11/2001 | Naggi et al. .................. 514/54 |

FOREIGN PATENT DOCUMENTS

| | | |
|---|---|---|
| DE | 39 17 251 | 11/1990 |
| DE | 44 10 876 | 3/1994 |
| EP | 0 278 100 | 8/1988 |
| WO | WO 93/09820 | * 5/1993 |
| WO | WO 93/24108 | 12/1993 |

\* cited by examiner

Primary Examiner—Gregory Huson
Assistant Examiner—Amanda Flynn
(74) Attorney, Agent, or Firm—Kenyon & Kenyon

(57) ABSTRACT

A multi-chamber renal dialysis container having at least two compartments and containing concentrated glucose in a first compartment and a hydrochloric acid solution containing electrolytes in a second compartment. The compartments are separated from one another during storage and transportation by separable peel seals, and the solutions can only be mixed with one another by the opening of the peel seals. An outlet of the multi-chamber container is separated by a further peelable seal, whereby a substantially empty third chamber is formed.

11 Claims, 1 Drawing Sheet

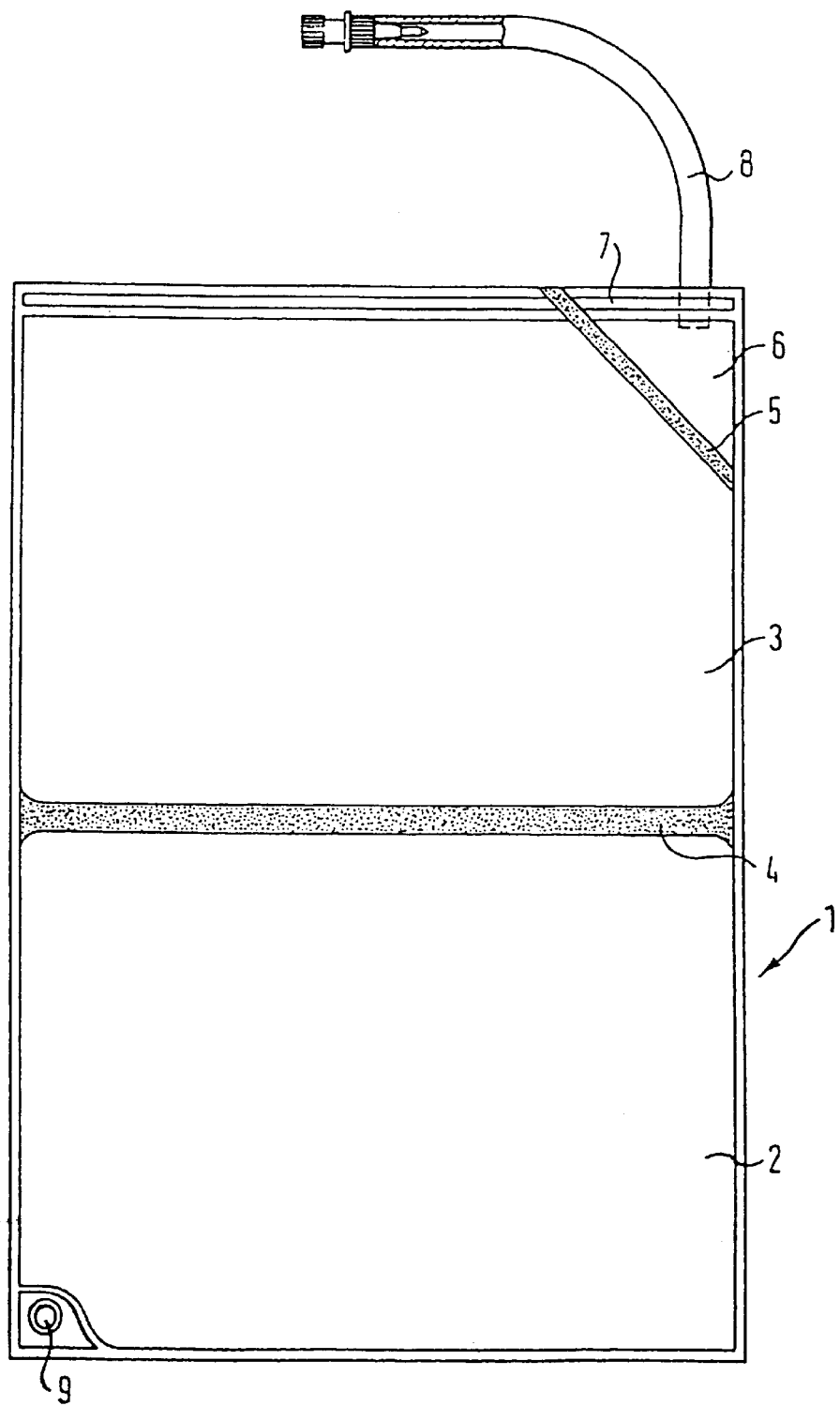

MULTI-CHAMBER CONTAINER WITH A CONCENTRATED GLUCOSE COMPARTMENT AND A CONCENTRATED HYDROCHLORIC ACID COMPARTMENT

FIELD OF INVENTION

The present invention relates to a multi-chamber container having at least two compartments for storing hemodialysis concentrates that, when diluted and mixed, serve to absorb toxic substances from the blood of patients suffering from renal disorders. More specifically, one compartment contains a first partial concentrate of glucose, and the other compartment contains a second partial concentrate of electrolytes and hydrochloric acid.

BACKGROUND OF THE INVENTION

Different types of multi-chamber containers are known, and are designed to hold different solutions in their compartments. While these solutions must be dispensed in mixed form, they are often storage incompatible. For this reason, the individual compartments of these multi-chamber containers are separated until just before the application of the solutions. In some cases, liquid communication channels are provided between the compartments, and are opened just prior to application so that the liquids can be mixed.

The fluid communication channel used in a multi-chamber container can be a breakable connector or a peelable seal, as described in German patent DE 44 10 876 C. The peelable seal opens as the result of pressure on the container so that the solutions can be easily mixed with one another in a single space, without dead volume. A typical application of such multi-compartment containers can be found in the field of renal dialysis, especially peritoneal dialysis, where solutions serve as the absorption medium for the body's toxic substances as a replacement for non-functional kidneys.

Such solutions comprise a buffer system, which is brought into the physiological region with an acid, and an electrolyte solution. Bicarbonate is a known buffer for blood. Accordingly, this buffer is generally chosen for hemodialysis solutions. Acetic acid is widely used as the acid, as it can be broken down in the citric acid cycle. To avoid any change in the vital electrolyte concentrations in the body of the patients, calcium ions and potassium ions, generally in the form of their chlorides, are added to the solutions. Also added are relatively high concentrations of common salt (NaCl). In general, glucose is used as the osmosis medium to generate the pressure which effects or at least accelerates the exchange of materials.

The separate storage of individual components that lack compatibility has been described in the prior art. German patent DE 39 17 251 C, for example, shows a two-chamber container system for the manufacture of a peritoneal dialysis solution, containing a concentrated acid solution with at least calcium ions in one chamber and a bicarbonate solution in a second chamber. In that reference, there is a risk of calcium carbonate, which is difficult to dissolve, being formed and precipitated in the solution if the components are stored together. For this reason, the calcium and the bicarbonate are stored separately and are only mixed just before being used in the procedure.

For the above reasons, it has become customary to store the bicarbonate separately from the other components of a hemodialysis solution. To save transportation and storage costs, it is also advisable to make the components available at the place of treatment in concentrated form when possible. For this reason, it has been proposed to provide the bicarbonate as a solid substance in a cartridge separate from all other components. See Patent Application No. EP 0 278 100 A. The NaCl is an easily soluble salt, and also lends itself to be provided in solid form, as a separate unit.

When the components are provided in powdered form, it is necessary to store the powders separately because if the powders are mixed fluctuations in concentration can arise in the course of the dissolving process due to different solubility rates. It is advantageous to provide the acid, the electrolytes and the glucose in a solid form. However, in practice, this is prevented by problems of solubility and dosage. On the one hand, the electrolytes are too hygroscopic and, on the other hand, acids such as conventionally used acetic acid are liquid at room temperature. For these reasons, the current procedure has been to make these components available as high concentration liquids to lower transportation costs.

It is also necessary to separate the components of solutions containing glucose, because the heat sterilization of such solutions can cause a breakdown of the glucose. Patent WO 93/09820 proposes to accommodate the glucose in a first compartment of a container in a solution having a glucose content of at least 10%, and provide a pH of around 3.5 by adding an acid. The breakdown of the glucose during sterilization of such mixture is thus prevented by the acid. The electrolytes and a lactate buffer can then be located in the second compartment of the container.

It has been found in the course of medical practice that acetic acid and other acids which can be broken down in the citric acid cycle show clinical side effects, for example, they can result in acidosis. For this reason, it has become customary to use acetate-free dialysis fluids. One physiologically compatible acid which is used in dialysis is hydrochloric acid. Hydrochloric acid is a strong acid, and is displaced when bicarbonate is introduced as the buffer system. This is because carbon dioxide can easily be formed during the mixing. Furthermore, hydrochloric acid has the disadvantage of not being heat-sterilizable, because HCl volatilizes too easily into a gas and has a highly corrosive effect.

SUMMARY OF THE INVENTION

The present invention relates to a container that provides a concentrated hemodialysis solution that allows acetate-free dialysis. The multi-chamber container in accordance with the invention comprises a flexible, biocompatible and transparent material, preferably made of polyolefins, and has a first compartment containing concentrated glucose and a second compartment containing concentrated hydrochloric acid, including calcium ions, magnesium ions and potassium ions and chlorides. The two compartments are separated by a peelable separating seal. The peelable seal is opened shortly before use by pressure on the two chambers, so that the two concentrates are mixed. A connection can also be placed between the two components. For example, a connector can be provided with a predetermined breaking point, which opens a liquid conduit upon being broken.

BRIEF DESCRIPTION OF THE DRAWING

The drawing shows an exemplary embodiment of a three-chamber container according to the invention.

DETAILED DESCRIPTION OF EMBODIMENTS OF THE INVENTION

According to an embodiment of the invention, a solution is formed where Hydrochloric acid is provided as the acid component, to allow an acetate-free dialysis. Since hydrochloric acid is a strong acid, its long-term storage together with glucose causes a decomposition of the solution. For this reason, storage together with glucose is not possible, and instead the hydrochloric acid is made available in accordance with the invention in a second compartment. Neither the acidified glucose solution—as described in WO 93/09820—nor the gaseous hydrochloric acid can be subjected to heat sterilization. For this reason, after the solution is manufactured in a sterile manner and is filled under conditions which are as sterile as possible, the container according to the invention is not subjected to any further sterilization.

In accordance with the present invention, the acid compartment can also contain the electrolytes calcium, magnesium and potassium. Optionally, common salt, NaCl, can be added to both the acid compartment and the concentrated glucose. In this manner, the transportation costs can be substantially reduced, due to the high concentration and resulting low volume of the products. Stocking at the point of use is also simplified. Furthermore, due to the reduced storage requirements, it is logistically possible to stock a selection of containers to provide an electrolyte concentrate individually adjusted for each patient.

Typically, a concentrate is concentrated 70–200 times, and more preferably 125 times. To achieve the concentration normally used for dialysis, the following composition can be used to obtain, for example, a 125 times concentrate:

| Solution A: | sodium chloride | 1,250 mM | |
|---|---|---|---|
| | potassium chloride | 500 mM | |
| | calcium chloride | 375 mM | |
| | hydrochloric acid | 750 mM | ph ≦ 1 |
| Solution B: | sodium chloride | 2,500 mM | |
| | glucose | 250 g/l | ph = 3 |

Each compartment of the container is preferably of equal size and can contain a quantity of 0.75 liters of concentrate. However, each compartment can also be of different size, to vary the mixing ratio between, for example, 1 and 3.

For illustration purposes, different mixing ratios and concentrations obtained are shown in tabular form below. Irrespective of how the concentrations or the mixing ratio are selected, the concentration ranges shown in Table 1 should be obtained in the finished solution.

TABLE 1

| Concentration ranges in the finished solution. | |
|---|---|
| NaCl: | 0–20 mM |
| KCl: | 0–4 mM |
| $CaCl_2$: | 1–2 mM |
| $MgCl_2$: | 0.25–075 mM |
| HCl: | 2–4 mM |
| Glucose: | 0.5–2 g/l (= 3–11 mM) |

The concentrations of the individual components can thus be in the ranges shown in Table 2.

TABLE 2

| Concentration ranges in the individual compartments. | |
|---|---|
| NaCl: | 0–4 M |
| KCl: | 0–800 mM |

TABLE 2-continued

| Concentration ranges in the individual compartments. | |
|---|---|
| $CaCl_2$ | 70–400 mM |
| $MgCl_2$: | 17.5–200 mM |
| HCl: | 140–800 mM |
| Glucose: | 100–400 g/l(= 0.6–2.2 M) |

The present invention further provides for the two concentrates to be mixed inside a storage container that has multiple chambers and a single outlet. To prevent the outlet from opening prematurely, the container can be also provided with a detachable closure. The closure can be, for example, a connector made of a material having a predetermined breaking point, so that a liquid conduit is opened when the pre-determined breaking point is reached. In a preferred embodiment, the closure includes a separating seal forming a third chamber of the container. In this embodiment the first compartment contains concentrated glucose, the second compartment contains concentrated hydrochloric acid and the third compartment is empty during storage and has an outlet in its end region.

The third compartment can be formed, for example, by the peel seal between the two compartments bifurcating into two branches at the lower end. For reasons of simplicity, however, a straight second peelable seal can be welded at one corner of the container, so that it separates a small region of the liquid compartment. The liquid is thus displaced back as far as possible into the liquid compartment. In a preferred embodiment, the separating seal can be located in the compartment containing the acid.

According to this embodiment, the separating means between the liquid compartments to be mixed are opened before the cut-off to the outlet opens. This can be achieved by the peel seals being of different length, or by controlling the strength of the seal, for example by varying the pressure and heat applied to the seal. For instance, the cut-off to the outlet can comprise a stronger adhesive than the separating means between the liquid compartments.

With reference to the drawing, an exemplary embodiment of a three-chamber container 1 made of flexible polymer material sealed at its periphery is described. The container 1 has three solution compartments. The first compartment 2 contains concentrated glucose while the second compartment 3 contains concentrated hydrochloric acid. A peelable seal 4 is located between the two solution compartments. The hydrochloric acid compartment has a further peelable seal 5 at its outer edge which separates a normally empty region 6 from the solution region. An outlet 8 such as a length of tubing leads to the mixing system of the dialyser, and is fitted to a peripheral seal 7. A hanging device 9 can be preferably provided on the edge of the container opposite the outlet edge.

What is claimed is:

1. A container for holding a medical concentrate for acetate-free renal dialysis, comprising:
   a first compartment containing a first partial concentrate comprising a glucose content of at least 10% (100 g/l);
   a second compartment containing a second partial concentrate comprising calcium, magnesium and potassium electrolytes in an acidic solution consisting of hydrochloric acid; and
   a first separating means disposed between the first and second compartments.

2. The container in accordance with claim 1, wherein the second partial concentrate containing electrolytes contains at least 2% (500 mM) hydrochloric acid.

3. The container in accordance with claim 2, wherein the second partial concentrate containing electrolytes contains 2.7% hydrochloric acid.

4. The container in accordance with claim 1, wherein the glucose content of the first partial concentrate is 20–30% (200–300 g/l).

5. The container in accordance with claim 4, wherein the glucose content of the first partial concentrate is 27% (270 g/l).

6. The container in accordance with claim 1, further comprising an initially empty third compartment, the third compartment being separated from the first and second compartments by a second separating means.

7. The container in accordance with claim 6, wherein the initially empty third compartment comprises an outlet disposed at an end region of the third compartment.

8. The container in accordance with claim 6, wherein the second separating means separating the third compartment comprises a stronger adhesive than an adhesive comprising the first separating means.

9. The container in accordance with claim 1, wherein the first separating means comprises a peelable seal.

10. The container in accordance with claim 1, wherein the electrolytes are individualized for a patient.

11. The container in accordance with claim 10, wherein the calcium electrolyte comprises 70 mM to 400 mM calcium chloride, the magnesium electrolyte comprises 17.5 mM magnesium chloride, and the potassium electrolyte comprises 0 mM to 800 mM potassium chloride.

* * * * *